United States Patent [19]

Galbraith et al.

[11] Patent Number: 5,276,498
[45] Date of Patent: Jan. 4, 1994

[54] ADAPTIVE SPATIAL FILTER FOR SURFACE INSPECTION

[75] Inventors: Lee K. Galbraith, Mountain View; John L. Vaught; Ralph C. Wolf, both of Palo Alto; Brian Leslie, Cupertino; Armand P. Neukermans, Palo Alto, all of Calif.

[73] Assignee: Tencor Instruments, Mountain View, Calif.

[21] Appl. No.: 882,047

[22] Filed: May 12, 1992

[51] Int. Cl.$^5$ .................................................. G01N 21/00
[52] U.S. Cl. ..................................... 356/237; 356/71; 250/550
[58] Field of Search .................. 356/71, 237; 250/550; 359/559

[56] References Cited

U.S. PATENT DOCUMENTS

| | | | |
|---|---|---|---|
| 3,658,420 | 4/1972 | Axelrod | 356/237 |
| 3,790,280 | 2/1974 | Heinz et al. | 356/239 |
| 3,972,616 | 8/1976 | Mimmi et al. | 356/237 |
| 3,981,562 | 9/1976 | Anthon | 356/239 |
| 4,480,899 | 11/1984 | Sprague | 350/356 |
| 4,557,563 | 12/1985 | Sprague | 350/162.12 |
| 4,560,994 | 12/1985 | Sprague | 346/108 |
| 4,766,324 | 8/1988 | Saadat et al. | 356/431 |
| 4,806,774 | 2/1989 | Lin et al. | 250/550 |
| 4,854,669 | 8/1989 | Birnbach et al. | 350/162.12 |
| 4,898,471 | 2/1990 | Stonestrom et al. | 356/394 |
| 4,988,153 | 1/1991 | Paek | 359/15 |
| 5,011,244 | 4/1991 | Smith et al. | 359/15 |
| 5,076,692 | 12/1991 | Neukermans et al. | 356/237 |
| 5,172,000 | 12/1992 | Scheff et al. | 356/237 |
| 5,177,559 | 1/1993 | Batchelder et al. | 356/338 |

Primary Examiner—Robert J. Warden
Assistant Examiner—Hien Tran
Attorney, Agent, or Firm—Schneck & McHugh

[57] ABSTRACT

An inspection apparatus for a light diffracting surface employs a planar array of individually addressable light valves for use as a spatial filter in an imaged Fourier plane of a diffraction pattern, with valves having a stripe geometry corresponding to positions of members of the diffraction pattern, blocking light from those members. The remaining valve stripes, i.e. those not blocking light from diffraction order members, are open for transmission of light. Light directed onto the surface, such as a semiconductor wafer, forms elongated curved diffraction orders from repetitive patterns of circuit features. The curved diffraction orders are transformed to linear orders by a Fourier transform lens. The linear diffraction orders from repetitive patterns of circuit features are blocked, while light from non-repetitive features, such as dirt particles or defects is allowed to pass through the light valves to a detector. Patterns of stripes can be recorded corresponding to the repetitive features of different integrated circuits. Different filters may be rapidly switched electronically in synchronization with a beam scanning a patterned surface inspecting different light diffracting patterns in different positions, allowing scattered or diffracted light from non-repetitive features to pass through the filter to a detector. A logical AND combination of two filters may be used so that two regions may be inspected in a single scan of the beam.

13 Claims, 10 Drawing Sheets

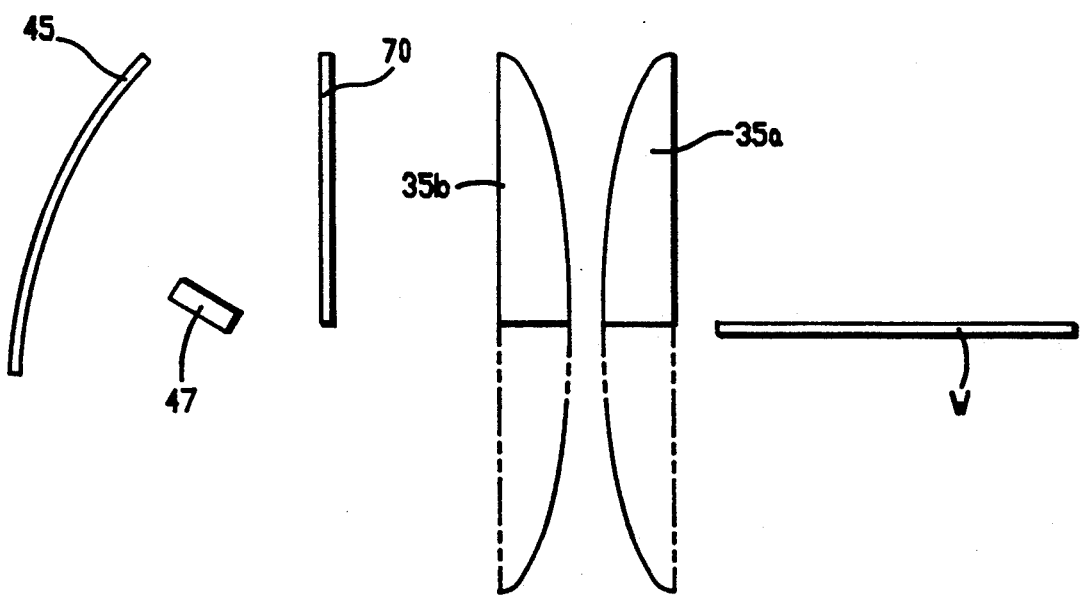
*FIG.—4a*
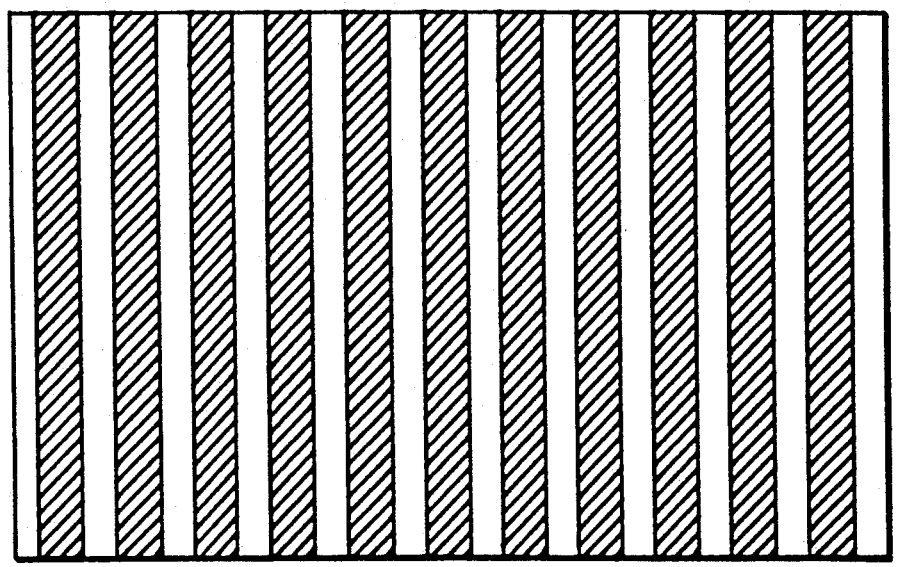
*FIG.—4b*

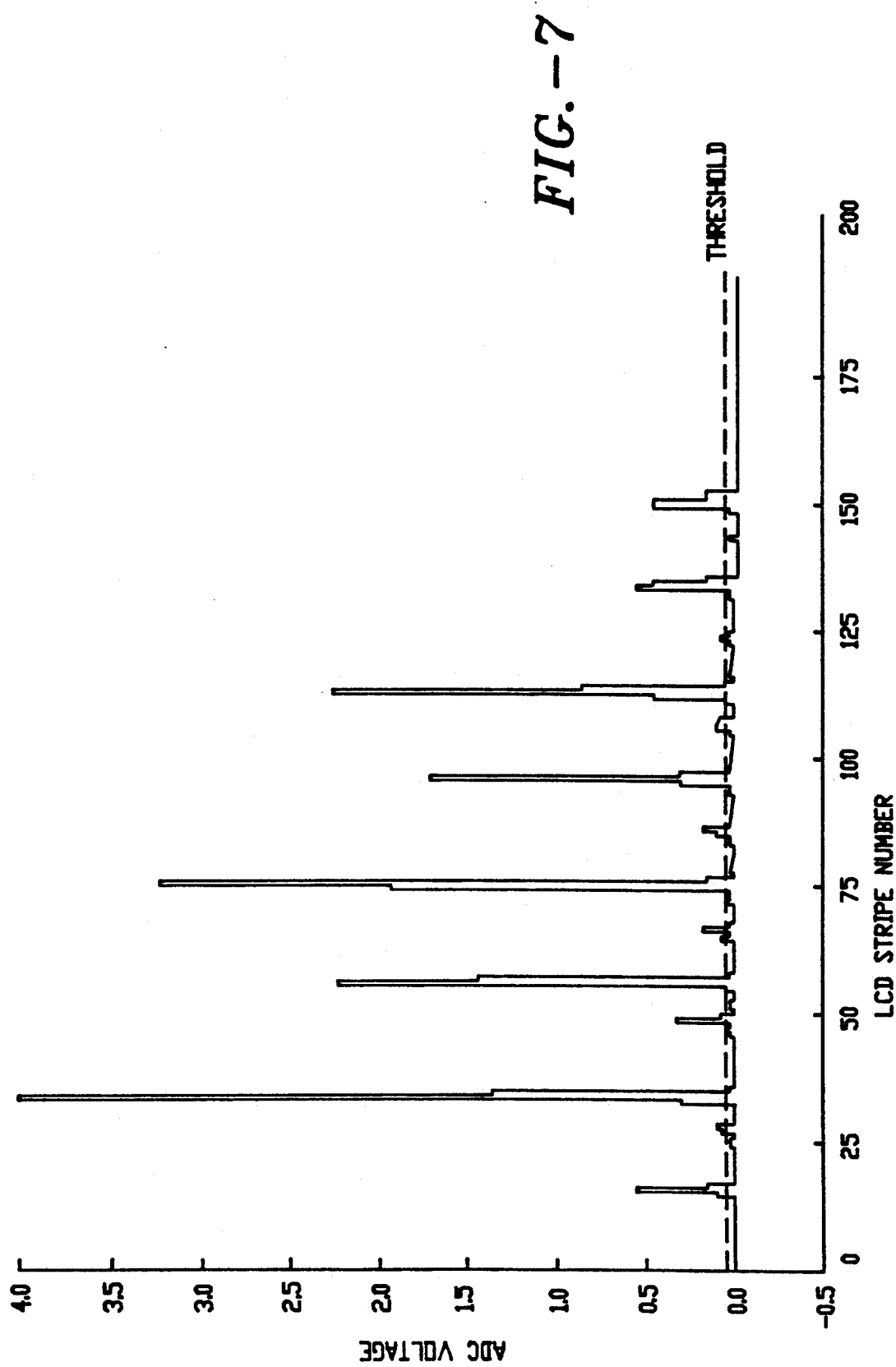
FIG.−7

ADAPTIVE SPATIAL FILTER FOR SURFACE INSPECTION

DESCRIPTION

1. Technical Field

The invention relates to optical inspection of patterned substrates and in particular to use of spatial filters for such inspection.

2. Background Art

In integrated circuit inspection, mainly on semiconductor wafers, as well as inspection of photomasks from which such circuits are made, it is known that periodic features of the objects give rise to diffraction patterns for light directed onto the objects. Inspection of patterned wafers should be distinguished from inspection of unpatterned wafers. In the latter case, scattering of light from the planar wafer surface is indicative of dirt particles or defects. Inspection of patterned wafers or surfaces is considerably more difficult because the topography of the circuit patterns themselves scatter light which is easily confused with dirt particles or defects. However, many wafers contain periodic structures and this periodicity may be used to separate light scattered from particles or defects. U.S. Pat. No. 4,898,471, to Stonestrom et al., assigned to the assignee of the present invention, teaches formation of electronic templates to separate signals from scattered light derived from periodic structures from light derived from non-periodic structures.

Another approach uses periodicity in a different way. In this approach diffraction patterns from periodic line patterns are filtered to find defects. For example, an array of memory cells in a single integrated circuit chip may have millions of transistors in a regular array. The array contains geometric patterns of closely spaced lines which serve to diffract light in much the same way as a reflective grating. The diffraction patterns can have multiple orders and the periodicity of the diffraction patterns allows one to observe non-periodic light scattering features which are interpreted as defects or dirt particles. While a direct image of the object is not formed, there is sufficient information in the diffracted light and the scattered light to form conclusions about the condition of the object, such as the amount and location of dirt particles. By blocking the diffracted light with a Fourier filter, only the light scattered by the non-periodic structures passes to a detector.

In prior application Ser. No. 832,379, assigned to the assignee of the present invention, J. Vaught et al. disclose use of a spatial filter which is used in the Fourier plane of a patterned wafer inspection apparatus. In that invention, a beam is focused onto the periodic features, through an optical system having a pinhole aperture stop, to produce, by diffraction, a plurality of spectral lines found in a plurality of spectral dispersion orders, with each order forming an elongated band. These elongated bands are blocked by opaque tracks on an otherwise transmissive filter. The light which is able to pass through the filter is light coming from defects or particles on the substrate. The filter is formed by placing photographic film in the Fourier plane and recording the bands with a sufficient exposure that adequate opacity will result when a negative image is developed. This negative image serves as a filter having a plurality of opaque tracks, corresponding to the bands mentioned above, in a transmissive field.

In U.S. Pat. No. 4,806,774 Lin et al. disclose a patterned wafer inspection system which employs a Fourier transform lens and an inverse Fourier transform lens positioned along an optic axis to derive an image pattern which can be selectively filtered to produce an image pattern of defects in the illuminated area of the wafer. In connection with FIG. 7 of the patent, a liquid crystal spatial filter is described which is a smectic light valve in which a Fourier transform pattern of the wafer is inscribed. The spatial filter comprises a pair of spaced-apart glass substrates that capture a smectic liquid crystal material between them. A laser beam is focused on an absorber layer within the structure locally heating the liquid by a sufficient amount above a critical temperature where a crystalline change occurs. When the heated material cools, when the beam is removed, the material scatters light in the heated zone, while non-heated material transmits light. In this way the filter pattern is permanently inscribed on the liquid crystal material and a Fourier filter is formed for wafer inspection. One of the benefits of the apparatus of Lin, as well as that of Vaught et al., is that relatively large areas of patterned wafers may be rapidly inspected.

As one might imagine, different circuit patterns give rise to the need for different Fourier filters because the periodicities are different and hence the diffraction patterns to be filtered are different. Each time a wafer with different circuit patterns is inspected, the inspection apparatus must be changed to accomodate the appropriate filter. This is not only time consuming, but gives rise to the possibility of error.

An object of the invention was to devise an inspection apparatus for patterned wafers with repetitive features which operates rapidly and reliably and which may be rapidly changed for different diffraction patterns.

SUMMARY OF INVENTION

The above object has been achieved by providing a wafer scanning inspection system with an adaptive Fourier filter which can be rapidly reconfigured for inspection of an entire wafer by a laser scanner or light beam, even when the wafer has different sections with different light diffracting properties. We have discovered that an array of individually addressable light valves based on liquid crystals will serve as an adaptive Fourier filter which may be configured to change as a beam scans different portions of a wafer, or even a chip, with different diffractive patterns requiring different filters. In contradistinction from filters which respond to illumination of large sections of a wafer, a laser scanner only illuminates a small section of a wafer, but with sufficient intensity to produce a characteristic Fourier diffraction pattern if closely spaced repetitive patterns exist, similar to an optical grating. Such line patterns exist in memory and logic arrays and similar circuits. Different portions of a wafer can have different Fourier diffraction patterns. The present invention adaptively responds to the different patterns in synchronization with the position of the beam.

For example, in a wafer scanning inspection, a scanning beam is directed at a low angle onto the wafer, striking a light diffracting pattern from periodic features of the wafer. The light which is diffracted and scattered from certain regions of the surface is collected by an optical system. Light diffracted from repetitive features appears in a hemispherical pattern or non-planar Fourier pattern. Lenses are used to transform this pattern into a planar pattern.

The non-planar Fourier pattern of diffraction spots is transformed into a plurality of quasi-parallel oblong spots in a plane, so that each spot becomes essentially one-dimensional. We have found that a planar array of light valves can adaptively form a Fourier filter for these spots. Moreover, this may be done with a scanning beam on the fly over a particular region of a wafer giving rise to a unique diffraction pattern and then changed as the beam scans another region giving rise to a different diffraction pattern. Fourier filters are formed by placing a planar array of individually addressable light valves, each valve slightly narrower than the spots, in proximity to the pattern. With the light valves closed and the beam scanning a first region of a wafer with repetitive line patterns giving rise to diffraction orders of light, the light valves are opened sequentially. When light passing through an open valve exceeds a threshold amount, the address of the valve is recorded. After this has been done for all light valves, those valves whose address has been recorded are kept closed, thereby blocking light in the pattern of collected diffracted light, except for light scattered from defects and particles. This scattered light is collected and analyzed in amplitude and position, then displayed, in a manner similar to bare wafer inspection devices. This procedure is repeated for different portions of a wafer where different diffraction patterns exist, in synchronization with the beam as the beam scans the wafer. Once particular filters are established for particular regions of a wafer, the filter patterns may be stored in a computer memory and recalled synchronously as the beam scans those regions. In this manner, the system "teaches" itself what filters are needed and what the filter configuration of the light valves is for particular regions of the wafer. Under computer control, the valves may be operated very rapidly. A plurality of filter patterns may be stored in a computer memory and called up as the beam comes upon different repetitive integrated circuit line patterns, each requiring a particular pattern for filtering diffraction orders arising from the periodic line patterns.

An integrated circuit chip having different structures with periodic features can have corresponding different Fourier filters introduced into an inspection system without intervention into the components of the optical system. These filters are provided very rapidly for an optical inspection system using a beam to scan a wafer for sub-micron size particles and larger size flaws.

BRIEF DESCRIPTION OF THE DRAWINGS

FIG. 4a is a side plan view of a lens doublet, illustrated in FIG. 1a, transforming a curved diffraction pattern from a hemispherical region of FIG. 2 to a straight parallel line diffraction pattern shown in FIG. 4b.

FIG. 4b shows a straight parallel line diffraction pattern, transforming the curved pattern of FIG. 3, using the doublet of FIG. 4a.

FIG. 4c is a side view of a single lens member of the doublet shown in FIG. 4a.

FIG. 7 is a plot of light intensity, measured at a detector, versus position of light diffracted by line patterns in a 1 Mb DRAM wafer, as measured in the Fourier transform plane.

BEST MODE OF CARRYING OUT THE INVENTION

Figure 1:
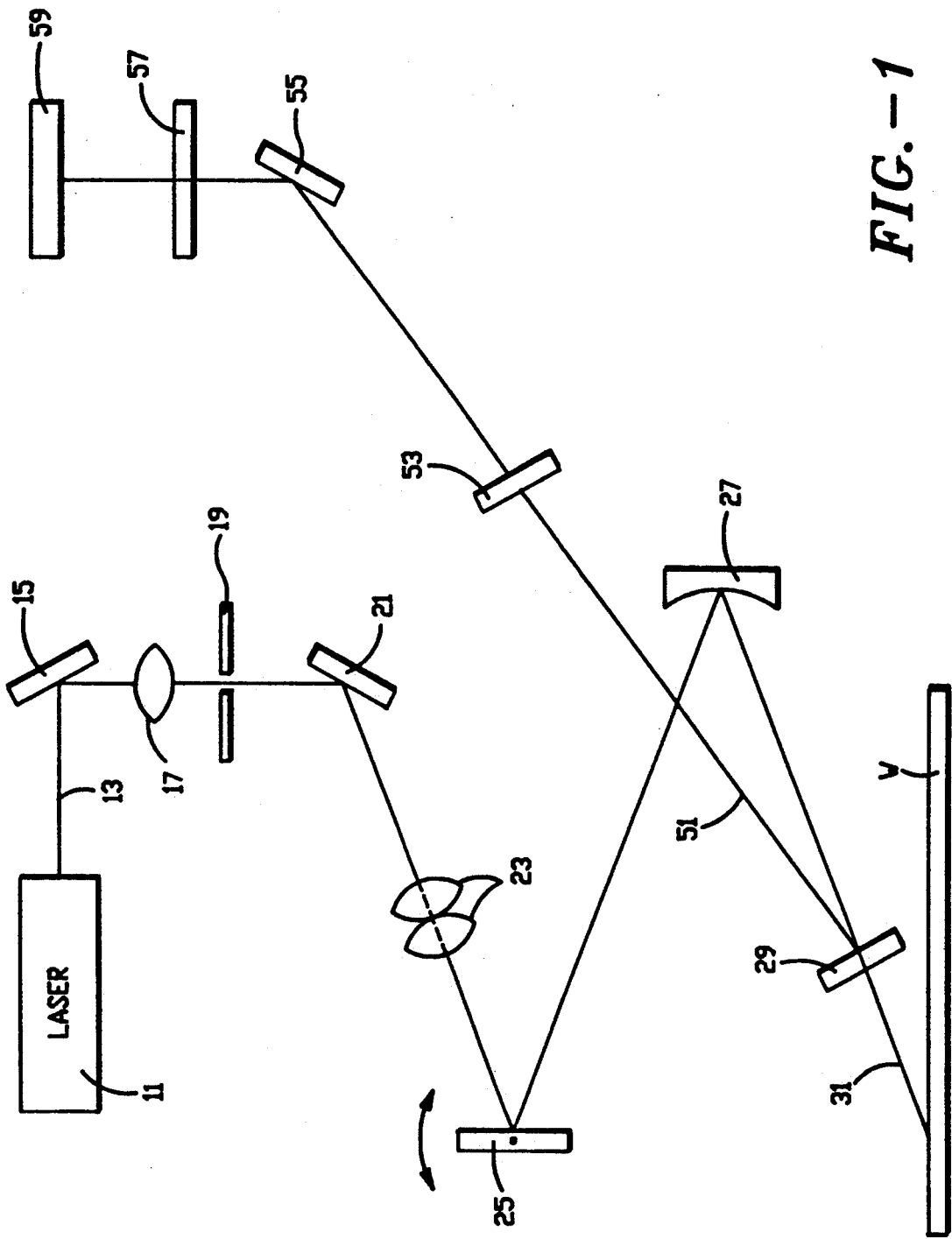
FIG. 1 is a plan view of the beam input stage of the apparatus of the present invention.
Figure 1A:
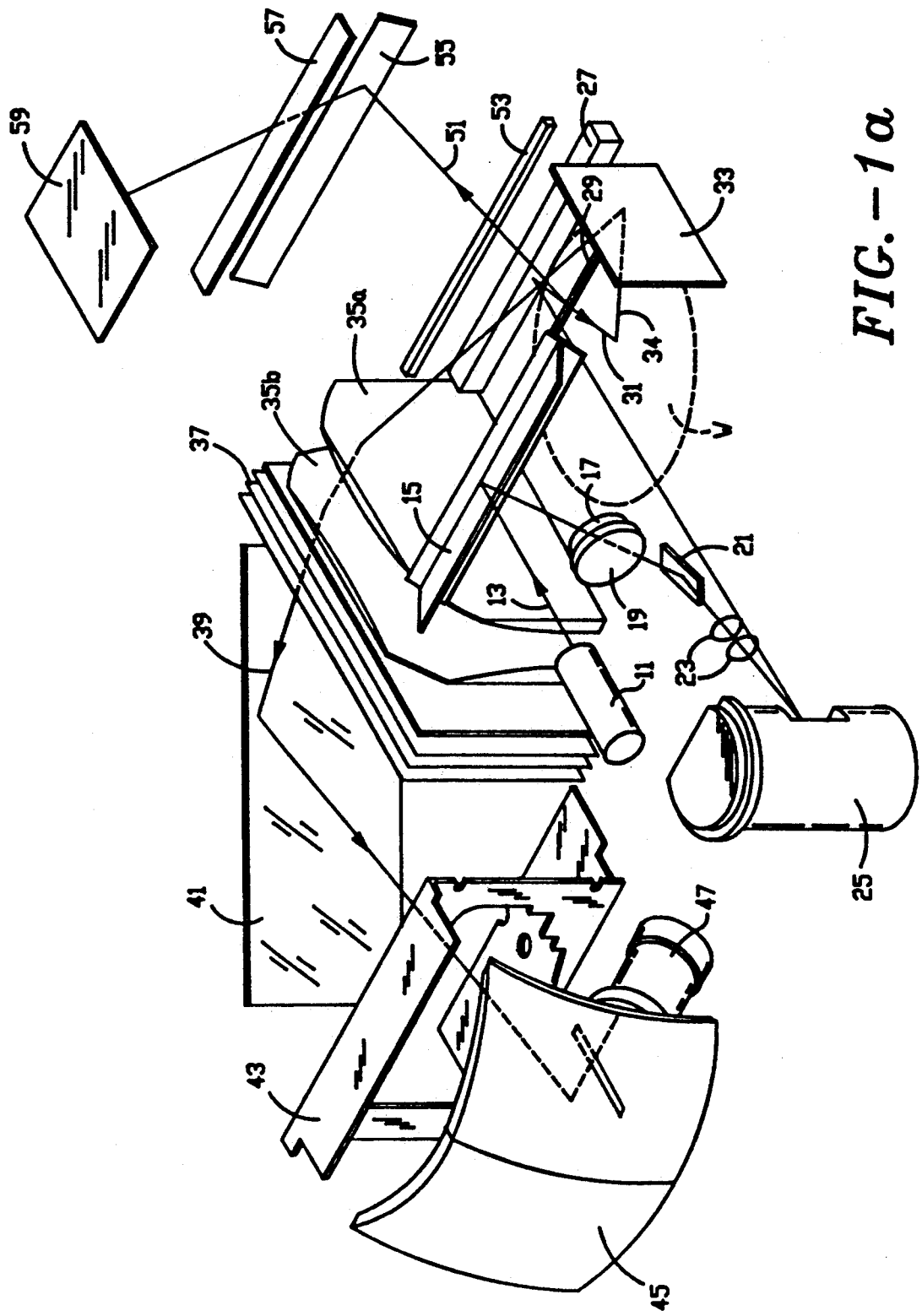
FIG. 1a is a perspective plan view of beam input and output stages of the apparatus of the present invention.

With reference to FIGS. 1 and 1a a wafer, W, is carried on a wafer chuck over a support, not shown, to the optical inspection station of the present invention. The wafer chuck and housing for the apparatus shown may be part of a cluster tool configuration where a robot arm moves a wafer through a number of different measuring, inspecting and processing steps. The present invention addresses the need for rapid inspection of entire wafers in such an environment, while providing intense illumination with a strong light source, such as a laser. Wafer W is patterned to have significant areas of repetitive or periodic surface topology. Such topology routinely occurs in the formation of large memory and gate arrays. Such arrays are typically rectangular and can occupy a significant portion of a chip or a wafer. The present invention is especially useful in those situations where a chip or wafer has mixed circuit portions including arrays with repetitive features and areas with non-repetitive features, such as discrete logic or the like.

The present invention has the ability to scan a wafer and provide an electronic spatial filter over those areas which have diffraction patterns formed by closely spaced lines in repetitive circuit patterns, such as memory cells, logic array circuits and the like. Motion of the scanning beam is synchronized with switching of the filter in place as described below.

The wafer W is illuminated by laser 11 which directs a beam 13 of monochromatic light, having a typical wavelength of 4800 Å, toward a mirror 15. The beam path is then directed through a lens 17 which focuses the beam and sends it through a filter 19 which is in the nature of a pinhole filter, passing the central portion of the beam and blocking peripheral regions of the beam. A mirror 21 redirects the beam toward scanner 25 after passing through focusing lenses 23. Scanner 25 is a commercial beam deflecting mirror driven by a resonant coil. Scanner 25 deflects the beam toward the field flattening mirror 27. Upon reflection, the beam passes through beamsplitter 29 which may be a single plate. Two beams emerge from beamsplitter 29.

A first beam 31 is directed onto wafer W where light scatters from the topographic features of the wafer. The scattered light travels at all angles, allowing collection from a side. The side view is not seen in FIG. 1, but is shown in FIG. 1a. Mirror 33 collects scattered and diffracted light, such as the diffracted ray 34 and directs the scattered light to the light collecting plano-convex doublet 35a, 35b. After passing through the doublet 35a, 35b, light passes through a series of polarizers 37 which select the polarization of the collected light. A collected ray 39 then impinges on mirror 41 where the light is directed to the focal plane stage 43 which supports the adaptive filter of the present invention, not shown. Assuming the collected ray passes through the filter, it is directed to a receiving mirror 45 which is spherical or parabolic in shape, directing light passing through the filter to a photomultiplier tube 47.

From the beamsplitter 29, there is a second path for light typified by ray 51 which may be seen in FIG. 1 as well as in FIG. 1a. The ray is rearwardly reflected through a glass element 53 having precise timing rulings thereon. The rulings provide a way to locate the beam as it scans across the wafer in order to synchronize the position of the scanning with placement of filters in position. Rulings may be counted from a starting point at the beginning and end of each scan. A method of synchronizing a scanning beam with marks on a wafer, similar to the rulings herein, is described in U.S. Pat. No. 5,083,035 to Pecen et al., assigned to the assignee of the present invention. Beam 51 then travels to a reflective mirror 55 where the beam changes direction and is directed through a Fresnel lens 57 and lens to a light detector 59. This second path employs no filter in front of detector 59.

Light, which is incident on repetitive features of a wafer, such as closely spaced lines associated with a memory or logic array, is essentially scattered in the same manner as a diffraction pattern. The light diffracting character of wafers and masks is known in the semiconductor industry and is frequently observed by the unaided eye. When a narrow laser beam is directed at a wafer the beam spot is round, with a beam diameter of about 25 micrometers but when the beam strikes the wafer from a low angle, say about ten degrees, the beam spot becomes elongated in one direction, but preserves its shape in the perpendicular direction. Light diffracted from the wafer will have an elongated character, because there are a few periods of repetitive line patterns in the width of the beam.

Figure 2:
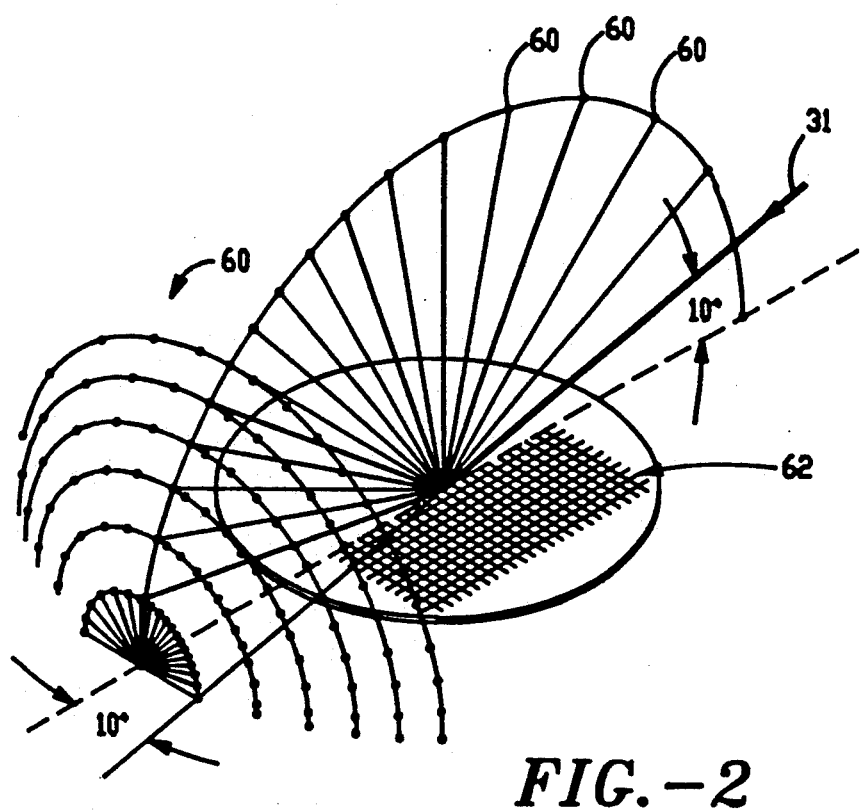
FIG. 2 is a three-dimensional diagrammatic view of a representative hemispherical diffraction pattern on a Fourier surface from identical line patterns on a portion of a semiconductor wafer.

FIG. 2 shows a three-dimensional array of diffraction spots which arise as the incoming light beam 31 impinges on an array of memory cells, A. The spots 60 are formed in space, on a hemispherical surface, by light diffracted from repetitive features of the wafer. The grid lines 62 on the wafer represent repetitive line patterns of circuits giving rise to light diffraction. The line patterns are greatly magnified and only exist where repetitive arrays of circuit elements exist. Diffracted light converges to spots 60 on a hemispherical surface. Lenses must be used to straighten a locus of spots into a planar configuration for more convenient use in imaging, such as projecting or filtering. Note that incident beam 31 comes in at a shallow angle, preferably about ten degrees.

In the evaluation of very rough surfaces, the angle of incidence could be reduced closer to grazing incidence and so the light collection angle could be reduced. In the preferred embodiment there is only a reduction in the collection angle using a curtain type filter described below. The reduced collection angle reduces scattering from non-periodic features, such as particles, but reduces even more scattering from the surface. This improves the signal-to-noise ratio for particle detection.

Figure 3:
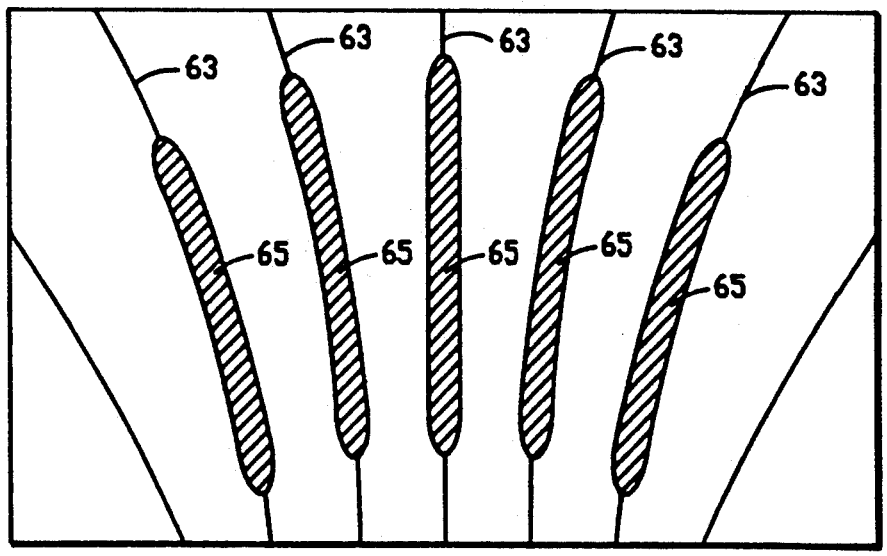
FIG. 3 shows a closeup view of the curved diffraction orders from a small hemispherical region of FIG. 2 flattened to a two-dimensional plane.

As mentioned previously, light scattered from the topographic features of the wafers is collected, as shown in FIG. 1a and directed to a light collecting doublet 35a, 35b. A regular lens would transform a portion of the hemispherical surface of diffraction spots, shown in FIG. 2 into a planar image, shown in FIG. 3. The spots become elongated, as depicted by diffraction members 65 and lie along curved trajectories 63, which are not visible. The curved spots of FIG. 3 would be difficult to filter with linear light valves. A transformation may be applied to the curved spots to convert the curved spots to linear spots with a Fourier transform lens. Such a lens works as follows. A regular photographic lens would convert all rays of incoming angle $\alpha$ to a position $x = f \tan \alpha$ in the Fourier plane, where "f" is the focal length of the lens. In the Fourier lens used here, all incoming rays of angle $\alpha$ are brought to a focus at a position $x = f \sin \alpha$. Although these differences are small for small angles $\alpha$, the resulting correction significantly removes the distortion of the diffraction spots. Using the doublet 35a, 35b, incorporating the transformation, the spots lie along straight trajectories as shown in FIG. 4b. These linear spots may now be filtered by appropriate linear light valves aligned in the same direction.

In FIG. 4a, there is a simplified view of the light collection optics. Wafer W diffracts light into the doublet 35a and 35b which are plano-convex lenses. These lenses have a distortion which converts the image of spots on an imaginary hemisphere to the diffraction orders seen in FIG. 4a. These doublet lenses may be determined by ray tracing for the particular geometry which is adopted. Returning to FIG. 4a, the doublet 35a, 35b focuses light to the transform plane 70 where the adaptive filter of the present invention is disposed in stage 43 shown in FIG. 1a. Light passing through the transform plane impinges on the parabolic or spherical mirror 45 and is focused into the PMT detector 47. Note that the doublet 35a and 35b consists of only one-half of a lens because light does not go through the lower half, so it need not be present.

Figure 4C:
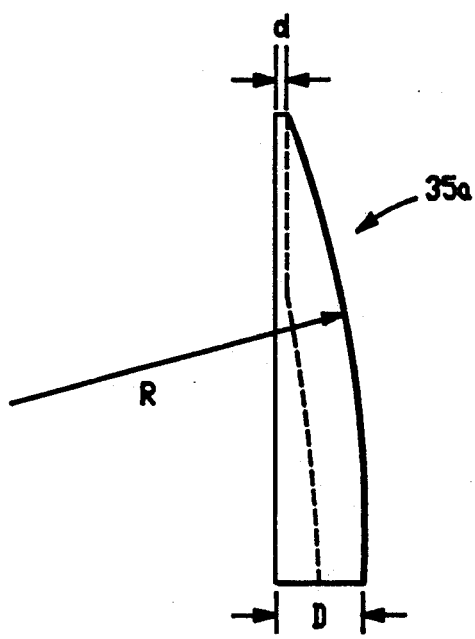
Figure 4D:
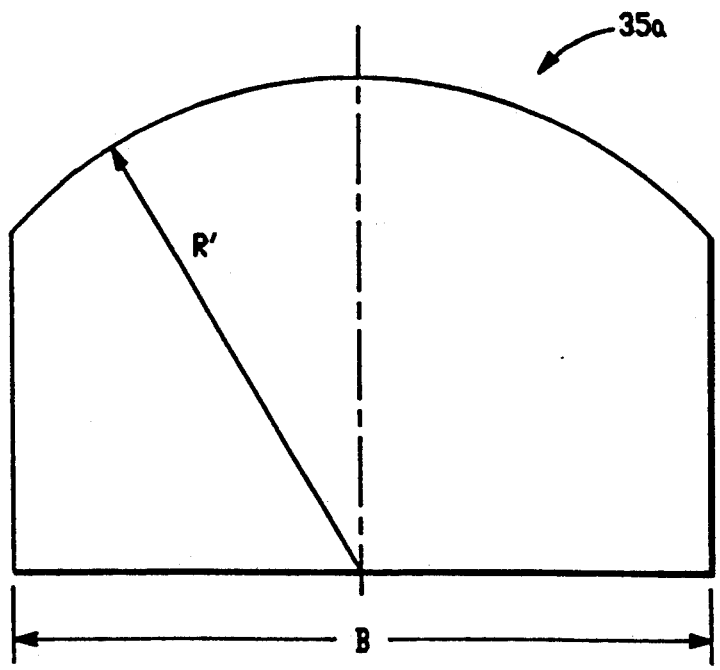
FIG. 4d is a front view of the lens shown in FIG. 4c.
Figure 4E:
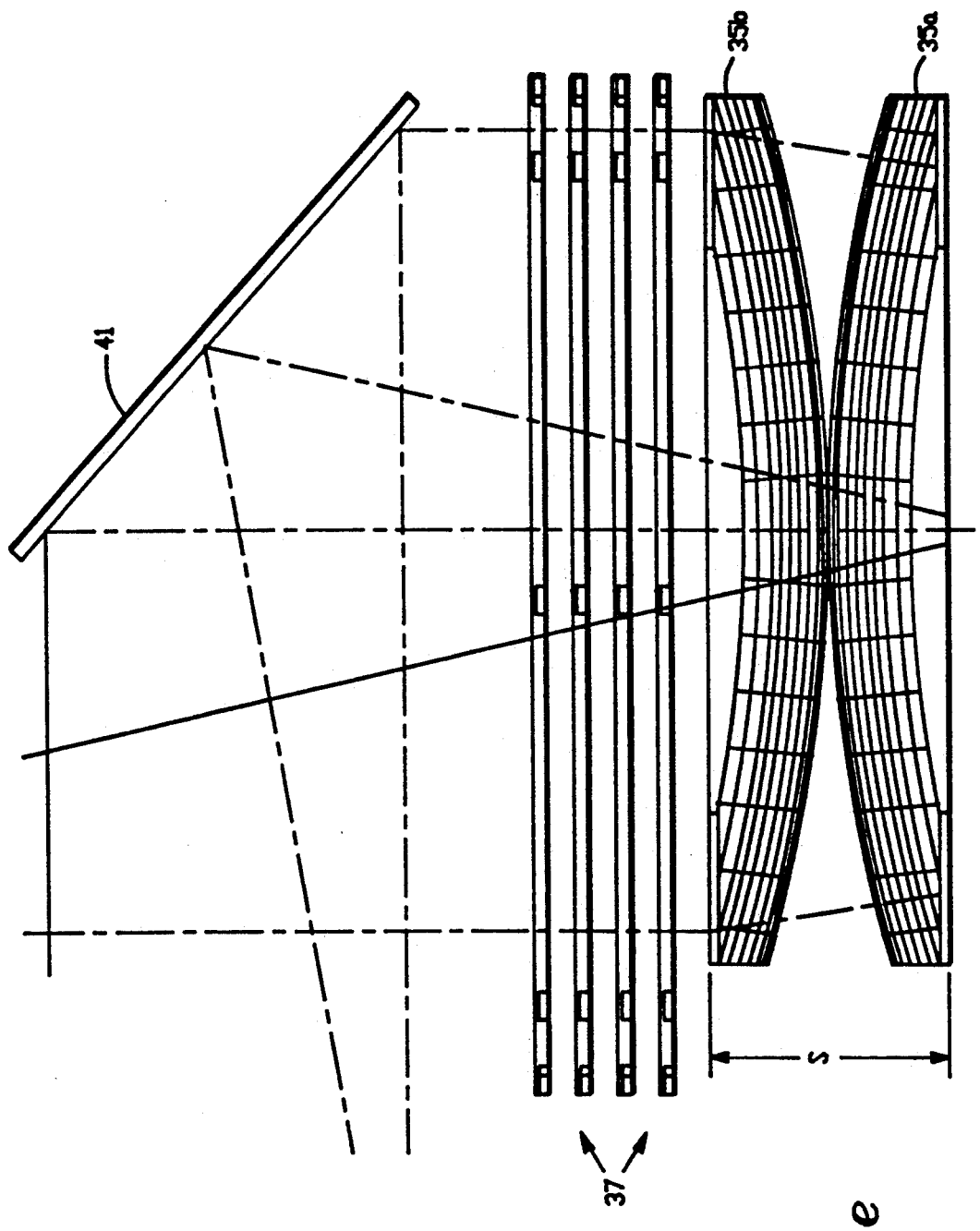
FIG. 4e is a top view of the doublet shown in FIG. 4a in combination with other optical elements.

In FIG. 4c the lens 35a of FIG. 4a is shown in more detail. The lens has a radius, R, of 17.10 cm. and a projected thickness dimension, d, at the top of 0.125 cm. with a projected thickness dimension, D, at the bottom of 1.212 cm. In FIG. 4d the base, B, of the lens 35a is 8.75 cm., while the radius, R', of the top of the piece, measured on the optical centerline 0.010 inches off of the piece is 6.0 cm. In FIG. 4e, the total front-to-back spacing, S, of the doublet is 2.42 cm. The separation of the two lenses is about 0.7 mm.

Figure 5:
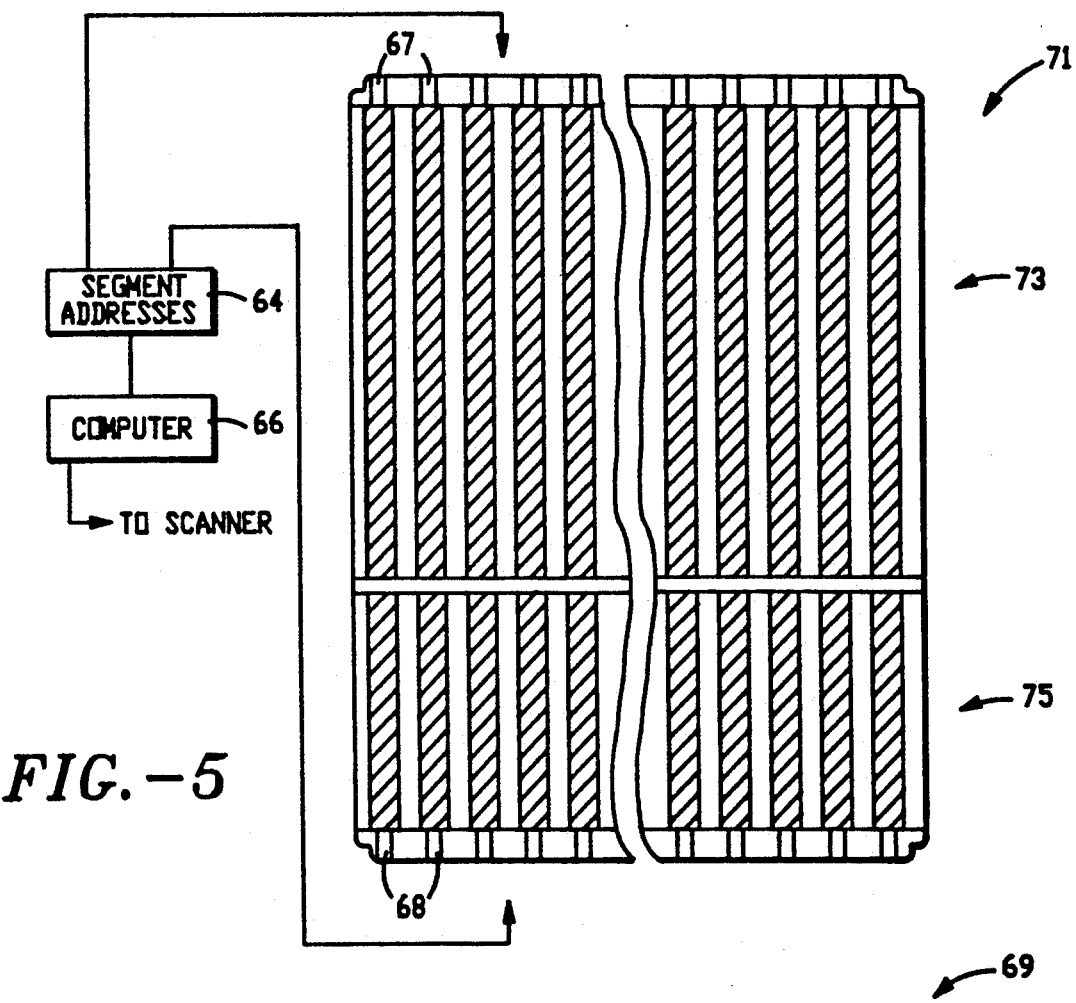
FIG. 5 is a front elevational view of a portion of a light valve array in accord with the present invention.

In FIG. 5, an array of light valves is shown. The array of valves consists of a rectangular panel 71 divided into individual upper segments 73 and lower segments 75. The upper segments are about twice the length of the lower segments, which is about one inch in length. Alternatively, single undivided segments could be used. Each upper segment and each lower segment of the array is driven individually by an electrode, in a manner similar to an LCD display of a digital timepiece. In such a timepiece it is common that numeric characters be formed by vertical segments, as well as horizontal segments. In a digital timepiece display, it is common that the vertical segments be divided into upper and lower portions, as in the present invention. In many instances, both the upper and lower segments will be operated together, although in some instances, as explained below, they will be operated separately by segment address circuits 64. The LCD segments are light valves which in the open mode transmit light and in the closed mode block light. Light valves of this type are commercially available under the trademark Taliq. Electrodes 67 and 68 apply voltages to the light valves for open and close control. A computer 66 has a memory which records and calls up desired segments in synchronism with the beam scanner.

There are three possible modes of operating the vertically split filter of FIG. 5. The first mode is that in which upper and lower vertical light valve segments are operated together, as if they were not split. This mode is selected where full height passage of light past the light valves yields a good, strong signal at the detector and stopping down of the aperture through the light valves does not substantially improve the signal-to-noise ratio of the system. The second mode is that in which all top segments are blocked, but all bottom segments are open, stopping the filter in a manner similar to dropping a curtain most of its height. This mode is mostly selected when scanning non-repetitive patterns giving rise to some diffraction, but not the well ordered diffraction which arises from repetitive line patterns. The third mode is that in which all top segments are blocked, but bottom segments are selected as in the first mode. This mode is selected where spatial filtering of diffraction orders from repetitive line patterns is desired, but wherein the signal-to-noise ratio of the output is enhanced by restricting the aperture of the receiver or detector.

Figure 5A:
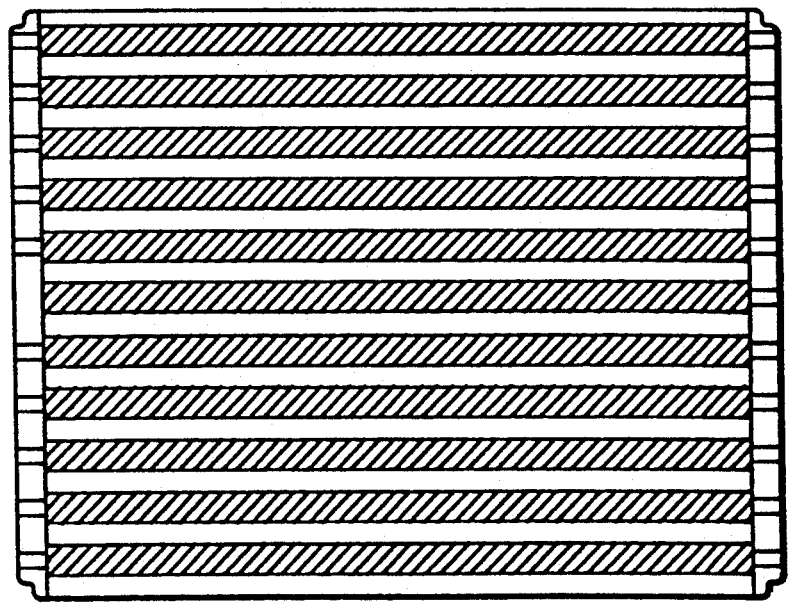
FIG. 5a is a front elevational view of an alternate embodiment of a light valve array in accord with the present invention.
Figure 8:
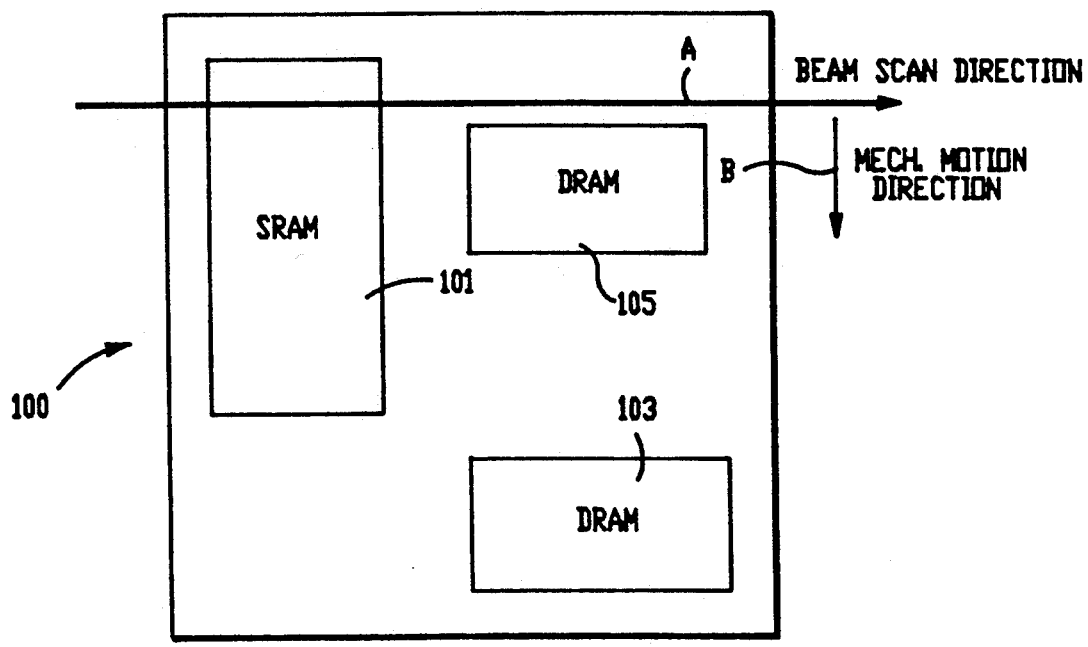
FIG. 8 is a top plan view of a large circuit chip having an SRAM circuit pattern and a DRAM circuit, both on the same integrated circuit chip.

In FIG. 5a, a horizontal alignment of light valves 69 is shown for a different kind of spatial filter. Here, no effort is made to align light valves with diffraction order members. Rather, the light valves are perpendicular or transverse with the diffraction order members. The light valves are operated like a curtain which descends from top to bottom in an adjustable manner. The effect of lowering the curtain is to simulate lowering the angle of the collection optics. This effect is especially good on rough surfaces or where a diffraction pattern from repetitive features is not available. Such a region could exist on a wafer between regions where diffraction patterns exist as shown in FIG. 8, discussed below. An opening in the curtain at the bottom is used for inspection of the non-repetitive or some types of repetitive pattern areas, especially areas having large amounts of light scattering. A light valve array which is 4 inches high by 6 inches wide might typically be stopped down to a filter one inch high by 6 inches wide in a continuously variable manner.

Figure 5B:
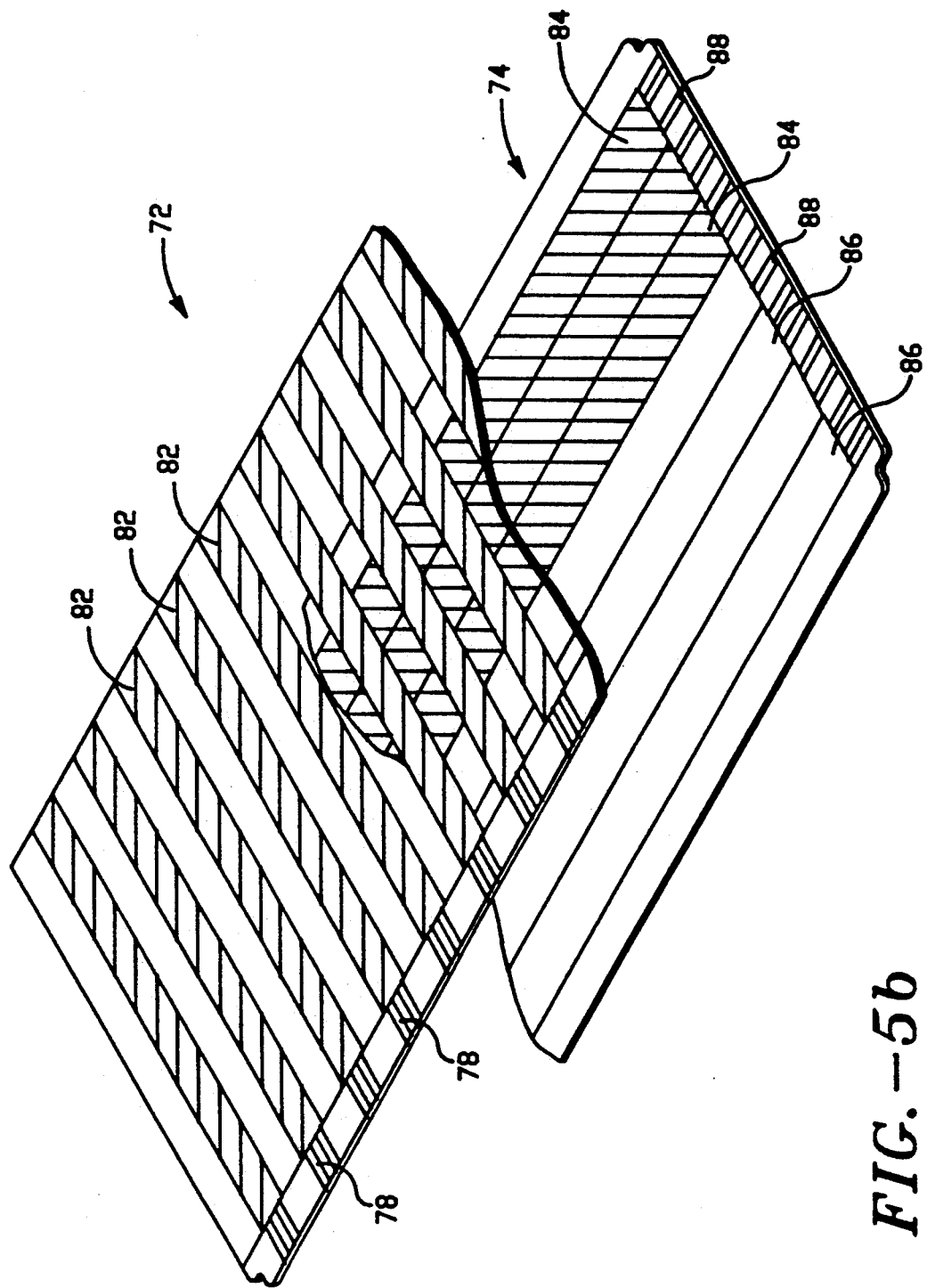
FIG. 5b is a perspective view of an alternate embodiment of the light valve array of FIG. 5.

In FIG. 5b a second array of light valves is placed directly behind the first array 72. The first array has a plurality of elongated, parallel light valves 82 which are individually addressable and controllable and which all extend in a first direction. The second array also has a plurality of elongated parallel light valves 84 and 86 which are individually addressable and which all extend in a second direction which is perpendicular to the first direction, as in FIG. 5a. The second array is used to selectively block portions of the first array. For example if light valves 84 of the second array 74 are closed and light valves 86 are open, then the lower half of array 72 is able to transmit light. The light valves of the second array 74 may be closed or opened like the curtain effect of FIG. 5a in order to stop down the first array to optimize the signal-to-noise ratio. Note that the valves of the first and second arrays are not split into segments, as in the upper and lower segments of FIG. 5. The function of the segments is now assumed by the valves of the second array which can permit as much or as little light from the first array to be transmitted as desired. While only a few valves are shown in each of the arrays 72 and 74, in practice scores of valves, perhaps a few hundred, would exist in each array to block diffraction orders. The edge contacts 78 for array 72 and edge contacts 88 for array 74 are connected to address circuits for selective activation of individual valves, such as by a computer. The combination of edge contacts, address circuits and computer form a means for activating the spatial filter to provide the desired filter pattern.

Figure 6:
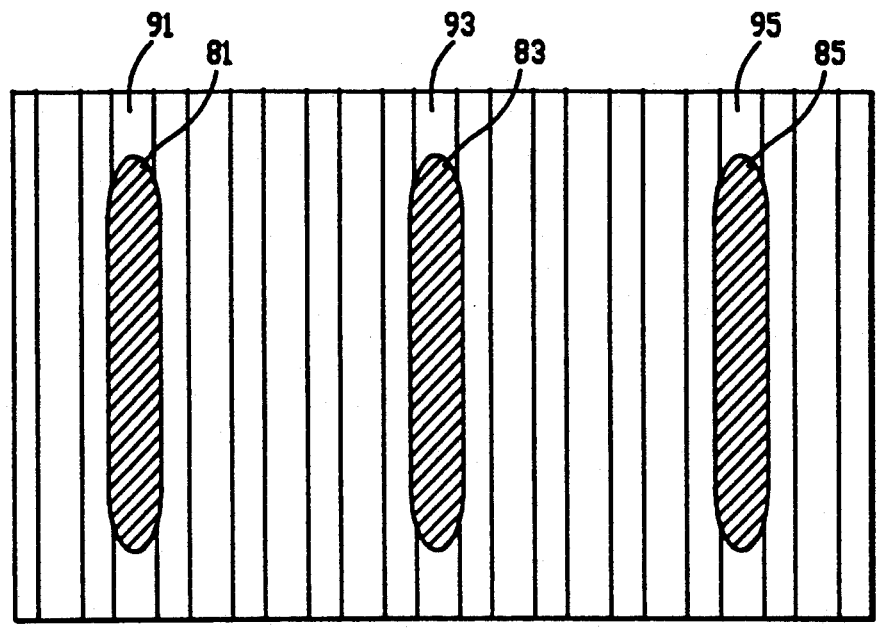
FIG. 6 is an elevational view of straight parallel line diffraction order members of the type shown in FIG. 4b superimposed on light valve array members of FIG. 5.

FIG. 6 shows how diffraction spots fall on the light valves of FIG. 5. The diffraction spots 81, 83 and 85 fall on corresponding light valves 91, 93 and 95. The light valves have a width which is typically narrower than the diffraction spot by about a factor of 3. It will be seen that the density of light valves substantially exceeds the density of the diffraction orders, but that both are in parallel alignment. The linear shape of the diffraction order lines makes them very suitable for filtration by the one-dimensional light valves, based on liquid crystals or other similar technologies. Since the LCD display is essentially one-dimensional, electronics for addressing the valves are similar to LCD electronics in digital timepieces, except that the number of vertical elements is substantially greater. The linear valves are substantially simpler to address than a two-dimensional arrangement. Use of two orthogonal linear arrays, as in FIG. 5a is still simpler than a two-dimensional arrangement in one array. Each light valve has a width on the order of about one-third the width of a Fourier spot or stripe, so three valves are used to block each spot. A small amount of useful light is blocked, but this small amount of light is compensated by higher contrast and simplicity of the one-dimensional array.

FIG. 7 shows a plot of the measured intensity pattern of a diffraction order when a beam scans a 16 Mb DRAM, with the peaks falling upon a panel of light valves. The valves are opened one at a time to measure light intensity through the valve. Intensity is measured by a voltage signal at the detector, with a total of 190 light valves.

To make an electronic filter, the valves are programmed to open and close sequentially while the beam scans a particular area of the wafer. At selected measurement points, when the beam is on the array areas the light transmitted through each valve stripe is measured, with all other stripes or valves closed. If the light exceeds a certain threshold, then the light valve will be closed during the filtering operation. If the light falls below a threshold setting, then the valve or stripe will be opened during actual use for circuit inspection. By sequentially opening the light valves one after another and performing the measurement while the beam is scanning, one learns the pattern of stripes which effectively blocks the light of the diffraction pattern from a DRAM or similar array of repetitive circuit features. Once the valve arrangement for blocking diffracted light is learned, all valves corresponding to the pattern can be closed simultaneously to block light under computer control, without visual observation or specific knowledge of the diffraction pattern. Once this pattern has been determined for a particular type of circuit or wafer, it can be stored in a computer memory and recalled whenever necessary.

When a beam is scanning over a wafer having both periodic arrays and random logic, it is necessary to distinguish between the two, since the filter of the present invention will not respond in the same way to random logic. The light pattern in the focal plane will change as it hits the various sections. However, it is desired to inspect only the periodic features of such wafers and therefore inclusion of light from other sections of the wafer, during formation of the spatial filter, is highly undesirable. This can be circumvented by gating the measurement of transmitted light. That is, the measurement of diffracted light through the valves of the filter is done only during the time that the beam is on the array area of interest. Although a valve may be open all the time, the value of light measured is only taken when the beam is in the array area of interest. This way, there is no influence from the random logic pattern. Beam position is known from the measurement grating previously described with reference to FIG. 1. During inspection time, the random logic areas are excluded, by ignoring data from those areas since the location of such areas is known.

Analogously, different filter patterns can be constructed which are appropriate for different arrays on the wafer by merely repeating the measurement process over the various repetitive areas of the wafer. Additionally, we form filters which are logical combinations of two filters, i.e. a pair of filters having closed valves ANDed together from each filter. Such a composite filter is useful when a single beam scan will traverse two areas, each having a characteristic spatial filter. It is usually not possible to change filters on a single scan of the beam when no mechanical motion of the wafer occurs. In this instance a first filter, filter A, is formed by scanning only one line pattern having diffraction orders, but not the second. Then a second filter, filter B, is formed by scanning only the second line pattern. Each filter comprises a series of addresses of light valves which must be closed to block diffracted light during a scan. The logical combination of filter A AND filter B means that more valves will be closed for scanning the first pattern than needed. The same applies for the second pattern and so some valuable light will be lost. However, the composite filter is a single filter which allows two areas with different repetitive line patterns, and dissimilar diffraction patterns, to be scanned on the same beam scan, thereby eliminating the need for separate scans for each area.

In FIG. 8, an ASIC chip 100 is shown having periodic areas 101 and 103. Area 101 may be an SRAM and area 103 may be a DRAM, the areas having diffraction properties, but both having repetitive structures, typically patterns of parallel lines, which give rise to two entirely different diffraction patterns. Two different spatial filters using light valves are constructed in the manner previously described, each one appropriate for the particular memory area. It is possible to scan the wafer twice, first with the DRAM filter in place, inspecting the DRAM area and then scanning the wafer again with the SRAM filter in place, inspecting the SRAM area. Between the SRAM and DRAM areas inspection circuitry using the addressable filters described herein is shut down, based upon the beam position if so desired. The beam scans back and forth horizontally as indicated by arrow A while the wafer is mechanically advanced as indicated by arrow B for a two-dimensional scan. Alternatively, it is possible to inspect both areas by dynamically changing the spatial filter during the time of advance of the wafer. During one scan, the DRAM filter is in place during the areas of DRAM inspection by a beam and the SRAM filter is switched in place when the beam starts scanning the SRAM area.

It takes approximately 10 msec to electrically switch valves and stabilize them. Since the wafer usually advances about 20 microns in 10 msec, it can be seen that the wafer does not travel very much during the valve switching time and hence the dynamic filter exchange can be done for areas of the wafer which are quite closely spaced. The number of filters is not restricted to two. More could be used if needed. Between periodic areas 101 and 103 dynamic filter exchange occurs in synchronization with the beam position and wafer advancement. Knowledge of the position of the periodic areas on the wafer is assumed, together with knowledge and control of wafer motion.

One filter which was implemented has 190 apertures in a width of 35 mils per aperture. Each stripe or valve is opaque when no voltage is applied to the strip and becomes transparent when 60 volts is applied to the electrodes. To avoid polarization of the strip, the voltage is periodically reversed at half the frequency of the laser scan. Voltage reversal is done at the end of a laser scan when the beam is not on the wafer to avoid interference with data collection.

When different areas 101 and 105, having different diffraction patterns, lie on the same scan line dynamic filter exchange is not possible and a logical combination filter of the type described above is used to block light diffracted from each area. Only a single filter is loaded with light valve addresses supplied by the computer. Scattered light from random defects or particles will pass through the filter.

As mentioned in connection with FIG. 5, the light valves may have top and bottom segments or may have portions blocked by an orthogonal array as in FIG. 5a. By blocking the upper field or a portion of it, one can reduce the aperture provided by the filter for the scanning of rough surfaces at low angles of the incident beam. If the beam stays at its usual angle, but the upper portion of the filter is closed, the light collection angle is effectively reduced. This can improve the signal-to-noise ratio for identifying particles or flaws on rough surfaces. It is also possible to block the upper half of the filter and block some of the valves in the lower part, combining both spatial filtering with the reduced aperture function described above. The filter is then made to act entirely similar to the filter covering the full field, although it is necessary to be able to drive the upper and lower segments individually.

The self-teaching or adaptive feature of the present invention is particularly useful. Wafers with unknown optical characteristics may be scanned with a beam and electronic filters formed in a short time. These filters can then be stored in a computer memory for future use with wafers of the same type. By means of computer control, the filters can be called up almost instantly without handling of the inspection equipment. Light which is not blocked from the filters is inferred to have originated from random sources, such as particles or flaws on the surface being inspected. The position of the beam is known and so the position of the particles or flaws is identified. Particle positions may be plotted on a display as described in U.S. Pat. No. 4,766,324, to S. Saadat et al., assigned to the assignee of the present invention.

Although semiconductor wafers have been described as the diffraction pattern generating surface, any surface yielding diffraction patterns to an inspection beam may be employed. This would include masks and finely etched surfaces or lined surfaces, such as optical recording media. The inspected surface may be partially light transmissive assuming the surface yields sufficient intensity in the diffracted pattern to produce signals at the detector in order to form the filters described herein.

We claim:

1. An optical surface inspection method comprising:
scanning a surface with a bean of light, said surface having repetitive light diffracting features, light diffracted from repetitive features in a first region of the surface forming a first light diffraction pattern which is different from a second light diffraction pattern formed by light diffracted from said repetitive features in a second region of the surface, said surface potentially also having random light scattering features, thereon, any light scattered by such random features in either of said first and second regions of the surface being superimposed upon said respective first and second light diffraction patterns, collecting light diffracted and scattered from the surface as said beam of light successively traverses said first and second regions of the surface, disposing a spatial filter in the path of light collected from the surface, said spatial filter having a plurality of individually electrically addressable light valves in an array, with a first filter pattern of on and off light valves in the array corresponding to said first light diffraction pattern for blocking light diffracted by said repetitive features in said first region of the surface and with a second filter pattern of on an off light valves in the array corresponding to said second light diffraction pattern for blocking light diffracted by said repetitive features in said second region of the surface, and first and second filter patterns being stored in a computer memory, activating said spatial filter in synchronism with the scanning beam traversing said first and second regions of the surface such that said first filter pattern is formed by said spatial filter when said beam of light is traversing and first region of the surface and said second filter pattern is formed by said spatial filter when said beam of light is traversing said second region of the surface, said spatial filter being activated by successively recalling said first and second filter patterns from said computer memory and applying selected electrical voltages to the array of light valves to open and close individual light valves of the array in accord with said respective filter patterns, said activated spatial filter blocking light diffracted from said repetitive features on the surface, while permitting light coming from random light scattering features on the surface to pass through open light valves of the spatial filter, and detecting light passing through said activated spatial filter.

2. The method of claim 1 wherein said filter patterns are determined by closing all light valves, moving the beam of light to selected locations in said first and second regions of the surface, for each said selected location successively opening and closing each light valve one at a time, measuring the amount of light passing through each light valve when open and recording the addresses of those light valves for which the measured amount of light exceeds a threshold amount, the filter pattern for each of said selected locations having light valves that are closed at each recorded address and open at all other addresses.

3. The method of claim 2 wherein filter patterns from a plurality of selected locations associated with a single sweep of the scanning beam are logically combined to form a single composite filter pattern for activation during that particular sweep of the beam.

4. The method of claim 1 wherein collecting said diffracted and scattered light included optically transforming curved diffraction order members of the collected diffracted light into a line pattern with a plurality of spaced apart, parallel, elongated, linear diffraction order members in a plane.

5. The method of claim 4 wherein disposing said spatial filter in the path of said light collected from the surface includes using a spatial filter in which the individual light valves in a one-dimensional array are in the form of linear stripes, and aligning the linear stripe light valves of the spatial filter with the parallel, elongated, linear diffraction order members of the line pattern.

6. The method of claim 5 further defined by disposing a second array of light valves behind said spatial filter, said second array of light valves being oriented transverse to the linear stripe light valves of the spatial filter, and closing selected light valves in said second array to intercept both diffracted and scattered light in a manner lowering the light collection angle and reducing an aperture through which the light passes.

7. The method of claim 1 wherein activating said spatial filter in synchronism with the scanning beam includes opening all light valves whenever said beam of light traverses any regions on the surface not having repetitive light diffracting features therein.

8. The method of claim 1 wherein activating said spatial filter includes reversing polarity of the electrical voltages applied to the array of light valves at the end of each scan, thereby avoiding polarization of the spatial filter.

9. An optical surface inspection apparatus comprising:
means for scanning a surface with a beam of light, said surface having repetitive light diffracting features such that light diffracted from said repetitive features form different light diffraction patterns when scanning different regions of the surface, said surface potentially also having random light scattering features, thereon, optical means for collecting light diffracted and scattered from the surface, a spatial filter disposed in the path of light collected from the surface, said spatial filter having a plurality of individually electrically addressable light valves in an array such that individual light valves are selectively opened and closed by the application of electrical voltages thereto in accord with a particular filter pattern, a computer memory storing a set of filter patterns therein corresponding to said different light diffraction patterns, said filter patterns being represented in said computer memory by addresses of those light valves that are closed for each of said filter patterns, means for activating said spatial filter in synchronism with the scanning beam traversing said different regions of the surface such that filter patterns are successively recalled from said memory and formed by said spatial filter so as to block diffracted light corresponding to the light diffraction pattern arising from each particular region of the surface that the beam successively traverses, said activated spatial filter permitting light coming from random light scattering features to pass therethrough;

means for detecting light passing through said spatial filter.

10. The apparatus of claim 9 wherein said optical means for collecting light includes lens means for optically transforming curved diffraction order members of the collected diffracted light into a line pattern with a plurality of spaced apart, parallel, elongated, linear diffraction order members in a plane.

11. The apparatus of claim 10 wherein said light valves in said spatial filter are in the form of linear stripes aligned parallel to said linear diffraction order members.

12. The apparatus of claim 11 wherein a second array of light valves is disposed behind said spatial filter oriented transverse to said light valves of said spatial filter.

13. The apparatus of claim 9 wherein at least one filter pattern stored in said computer memory is a composite filter pattern formed from the logical combination of plural filter patterns associated with a single sweep of the scanning beam.

* * * * *

UNITED STATES PATENT AND TRADEMARK OFFICE
CERTIFICATE OF CORRECTION

PATENT NO. : 5,276,498
DATED : January 4, 1994
INVENTOR(S) : Lee K. Galbraith et al.

It is certified that error appears in the above-indentified patent and that said Letters Patent is hereby corrected as shown below:

Claim 1, column 11, line 20, "from repetitive features" should read - - from said repetitive features - -.

Claim 1, column 11, line 42, "on an off" should read - - on and off - -.

Claim 1, column 11, line 45, "and first and" should read - - said first and - -.

Claim 1, column 11, line 52, "is traversing and first region" should read - - is traversing said first region - -.

Claim 4, column 12, line 19, "included" should read - - includes - -.

Signed and Sealed this

First Day of November, 1994

Attest:

BRUCE LEHMAN

*Attesting Officer*  *Commissioner of Patents and Trademarks*